US006270739B1

(12) United States Patent
Barnicki et al.

(10) Patent No.: US 6,270,739 B1
(45) Date of Patent: *Aug. 7, 2001

(54) PROCESS FOR THE REMOVAL OF CARBON DIOXIDE FROM 3,4-EPOXY-1-BUTENE PROCESS RECYCLE STREAMS

(75) Inventors: Scott Donald Barnicki; John Robert Monnier, both of Kingsport, TN (US); Jerome Leonard Stavinoha, Jr., Longview, TX (US); Robert Sterling Kline, Talbott; Gary Wayne Hartley, Kingsport, both of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/596,246

(22) Filed: Jun. 16, 2000

(51) Int. Cl.$^7$ .................................................. C01B 31/20

(52) U.S. Cl. .......................................... 423/229; 423/228

(58) Field of Search ..................................... 423/229, 228

(56) References Cited

U.S. PATENT DOCUMENTS

| | | |
|---|---|---|
| 3,137,654 | 6/1964 | Johnson et al. . |
| 4,440,731 | 4/1984 | Pearce . |
| 4,477,419 | 10/1984 | Pearce et al. . |
| 4,879,396 | 11/1989 | Ozero . |
| 4,897,498 | 1/1990 | Monnier et al. . |
| 4,950,773 | 8/1990 | Monnier et al. . |
| 5,117,012 | 5/1992 | Stavinoha, Jr. et al. . |
| 5,138,077 | 8/1992 | Monnier et al. . |
| 5,312,931 | 5/1994 | Stavinoha, Jr. . |
| 5,362,890 | 11/1994 | Stavinoha, Jr. et al. . |
| 5,618,954 | 4/1997 | Boeck et al. . |
| 5,756,779 | 5/1998 | Stavinoha, Jr. . |
| 5,904,908 | * 5/1999 | Suzuki et al. ................. 423/228 |
| 6,036,931 | * 3/2000 | Yoshida et al. ............... 423/228 |
| 6,165,433 | * 12/2000 | Chakravarti et al. .......... 423/229 |
| 6,207,121 | * 3/2001 | Rooney ........................ 423/228 |

FOREIGN PATENT DOCUMENTS

19828977 A1   6/1998   (DE) .

OTHER PUBLICATIONS

Tennyson, R.N. and Schaaf, R.P., The Oil and Gas Journal, 78–86, Jan. 10, 1977.
Zomerdijk, J.C. and Hall, M.W., Technology for the Manufacture of Ethylene Oxide, Catal. Rev. –Sci Eng. 23 (1&2), 163–185 (1981).
Kirk–Othmer Encyclopedia of Chemical Technology, 4th Edition, vol. 9, "Ethylene Oxide", 924–938 (1994).
Ozero, B.J. and Landau, R., "Ethylene Oxide", Encyclopedia of Chemical Processing and Design, vol. 20, 284–297, (1984).
Kohl and Riesenfeld, Gas Purification, $4^{th}$ Edition, 129–133, 184–187, 211–238 (1985).
Lees, F.P., "Loss Prevention in the Process Industries", vol. 1 485–486 (1980).
Coffee, R.D., "Loss Prevention 13", 74–80, (1980).
Kister, H.Z., Distillation Design, McGraw Hill, New York (1992).

* cited by examiner

*Primary Examiner*—Deborah C. Lambkin
(74) *Attorney, Agent, or Firm*—Matthew W. Smith; Harry J. Gwinnell

(57) ABSTRACT

Disclosed is a process for the efficient removal of carbon dioxide from a gas recycle system generated in an epoxidation process wherein 1,3-butadiene is selectively oxidized to 3,4-epoxy-1-butene. Carbon dioxide at low partial pressure is absorbed into an alkanolamine solution from a low pressure recycle gas stream containing high levels of oxygen. Also disclosed is a means for reclaiming the alkanolamine from a solution of a carbon dioxide-alkanolamine salt or adduct formed in the carbon dioxide removal process.

24 Claims, 2 Drawing Sheets

US 6,270,739 B1

PROCESS FOR THE REMOVAL OF CARBON DIOXIDE FROM 3,4-EPOXY-1-BUTENE PROCESS RECYCLE STREAMS

INTRODUCTION

This invention pertains to a process for the removal of carbon dioxide from recycle streams produced in processes wherein 3,4-epoxy-1-butene (EpB) is produced by the silver-catalyzed, vapor-phase oxidation of 1,3-butadiene. More specifically, this invention pertains to the removal of carbon dioxide from EpB process streams by contacting the carbon dioxide-containing stream with solution containing one or more unsaturated or saturated amino alkyl alcohols (hereafter referred to as alkanolamines).

BACKGROUND OF THE INVENTION

Processes for the production of EpB by the selective epoxidation of 1,3-butadiene in the presence of a modified silver catalyst are described in U.S. Pat. Nos. 4,897,498, 4,950,773, 5,138,077 and 5,362,890. The feed to the epoxidation zone comprises butadiene, an oxygen-containing gas and an inert diluent gas in various proportions. The gaseous epoxidation effluent typically comprises EpB, butadiene, oxygen, inert gas and a mixture of reaction by-products comprising water, carbon dioxide, acrolein, furan, vinylacetaldehyde and crotonaldehyde. After removal of the EpB product, e.g., as described in U.S. Pat. No. 5,117,012, most or all of the epoxidation effluent gas is recycled to the epoxidation zone. During the epoxidation process, some of the reactant butadiene and/or product EpB is decomposed to carbon dioxide and water. If not removed, the carbon dioxide will increase in the epoxidation effluent recycle stream, i.e., to at least 2 mole percent or more, affecting detrimentally the efficiency of the silver-catalyzed oxidation. For example, when using an epoxidation feed comprising butadiene, an oxygen-containing gas, an inert diluent gas and approximately 2 mole percent carbon dioxide, the EpB production rate can be reduced by as much as 50 percent as compared to a substantially identical epoxidation feed containing 0.002 mole percent carbon dioxide. Therefore, it is desirable, if not essential, that an EpB production facility includes means for the removal of $CO_2$ from the epoxidation recycle gas stream.

In *Kirk-Othmer Encyclopedia of Technology*, 4th Edition, "Ethylene Oxide", 930–933 (1994), Dever et al. disclose that the standard gas-phase epoxidation process for the production of ethylene oxide from ethylene with pure oxygen is operated at a pressure of 2–3 MPa (290 to 435 psia) and that the recycle gas contains 5–10 mole percent carbon dioxide. Dever et al. further state that at carbon dioxide concentrations above 15 mole percent, catalyst activity is adversely affected. In such a process, the carbon dioxide partial pressure in the recycle gas is maintained at 0.1 to 0.3 MPa (14.5 to 43.5 psia) by contacting the ethylene oxide absorber off-gas with a carbon dioxide-absorbing solution in a second absorber. Zomerdijk and Hall, Cat. Rev. —Sci. Eng., 23(1&2) 163–185 (1981), Ozero, U.S. Pat. No. 4,879, 396, and Ozero and Landau, *Encyclopedia of Chemical Processing and Design*, "Ethylene Oxide" 289–290 (1984) all teach that contact of the recycle gas with a hot potassium carbonate solution is the standard means for the removal of carbon dioxide from ethylene oxide plants.

As is disclosed by Kohl and Riesenfeld, *Gas Purification*, 4th Edition, 211–238 (1985), in such a process with the above-cited carbon dioxide partial pressures, the carbon dioxide-laden recycle gas typically is contacted with a lean hot potassium carbonate solution in a countercurrent absorption tower. The carbon dioxide in the gas reacts with the potassium carbonate solution in the absorber and is removed as a carbon dioxide-rich liquid stream from the bottom of the absorber. The chemically-bound carbon dioxide is stripped from the rich carbonate solution by a combination of heat and pressure changes and the lean absorber solution is recycled to the carbon dioxide absorber. For vapor phase, ethylene oxide production, carbon dioxide removal requirements for maintaining reactor productivity are not very demanding. The carbon dioxide removal system must be able to reduce the carbon dioxide concentration in the recycle gas stream from a feed partial pressure of around 0.1 MPa to 0.45 MPa (14.5 to 65.3 psia) to an outlet carbon dioxide partial pressure of at most 0.1 MPa to 0.3 MP (14.5 to 43.5 psia).

Tennyson and Schaaf, *Oil & Gas J.*, 78–86 Jan. 10, (1977), disclose that the most economical process for achieving such carbon dioxide removal efficiencies given the above carbon dioxide absorber feed partial pressures and desired outlet carbon dioxide partial pressures is hot potassium carbonate solutions. Tennyson and Schaaf also state that below about 0.069 MPa (10 psia) carbon dioxide partial pressure in the feed gas to the carbon dioxide absorption system, hot potassium carbonate solutions become uneconomical for achieving carbon dioxide outlet partial pressures of about 0.002 MPa (0.3 psia), a level much lower than required for ethylene oxide production. Moreover, physical solvents for carbon dioxide absorption such as methanol, N-methylpyrrolidinone, and water are unsuitable for such demanding carbon dioxide removal requirements.

U.S. Pat. No. 5,312,931 discloses that the gas-phase epoxidation process for the production of 3,4-epoxy-1-butene (EpB) from 1,3-butadiene with pure oxygen is operated at a pressure of 0.2–0.9 MPa (29 to 130.5 psia) with 4 to 25 mole percent oxygen in the reactor feed (0.012 to 0.25 MPa—1.74 to 36.25 psia oxygen partial pressure), and that most preferably the recycle gas contains less than 0.5 mole percent carbon dioxide (typically 0.001 to 0.004 MPa carbon dioxide partial pressure). Thus, the carbon dioxide removal requirements for the recycle system in EpB production are much more stringent than ethylene oxide production, and outside of the normal economic range of the typical hot potassium carbonate system.

Kohl and Riesenfeld, *Gas Purification*, 4$^{th}$ Edition, 184–186 (1985), disclose that aqueous solutions of sodium hydroxide or potassium hydroxide can be used to reduce carbon dioxide levels in gas streams to very low levels, e.g., as low as 1 part per million by volume (ppmv) regardless of inlet carbon dioxide partial pressure. The sodium or potassium hydroxide reacts with the dissolved carbon dioxide to form heat-stable salts which cannot be decomposed at economical pressures and temperatures to regenerate the alkali metal hydroxide. Thus, the alkali metal hydroxide solutions cannot be recycled and large amounts of aqueous alkali hydroxides must be purchased and waste salt stream must be discarded, making such a process uneconomical for bulk removal of carbon dioxide such as for a butadiene epoxidation process.

Tennyson and Schaaf, *Oil & Gas J.*, 78–86 Jan. 10, (1977), disclose that alkanolamine solutions such as monoethanol amine (MEA) can be used to achieve economically very low carbon dioxide outlet partial pressures, e.g., 0.00069 MPa—0.1 psia or lower, with feed carbon dioxide partial pressures in the same range or higher. Kohl and Riesenfeld, *Gas Purification*, 4$^{th}$ Edition, 129–133 (1985), disclose that such alkanolamine solutions are very susceptible to oxidative degradation and that oxygen should be excluded rigorously from the carbon dioxide absorber feed gases. Further evidence of the perceived detrimental effects of oxygen on alkanolamine solutions is presented in U.S. Pat. No. 3,137,654. This patent discloses that even a small amount of oxygen in a MEA solution will lead to oxidative degradation of the MEA and release of the degradation product ammonia into the carbon dioxide absorber outlet gas. Moreover, the degradation products of MEA and other alkanolamines were found to promote corrosion of the absorber and related equipment when constructed of less expensive carbon steel.

For removal of carbon dioxide from streams such as flue gases containing relatively low levels of oxygen, U.S. Pat. Nos. 4,440,731 and 4,477,419 disclose methods of reducing oxygen-induced degradation and corrosion by the addition of copper salts to the alkanolamine solutions. Such flue gases typically contain 2–5 mole percent oxygen at atmospheric pressure, e.g., oxygen partial pressures of 0.002 MPa to 0.005 MPa—0.29 to 0.73 psia, an order of magnitude lower oxygen partial pressure (e.g., about 0.056 MPa—8 psia) than the typical recycle gas in a vapor phase EpB process as disclosed in U.S. Pat. Nos. 5,312,931 and 5,362,890.

BRIEF DESCRIPTION OF THE DRAWINGS

Accompanying

BRIEF SUMMARY OF THE INVENTION

Figure 1:
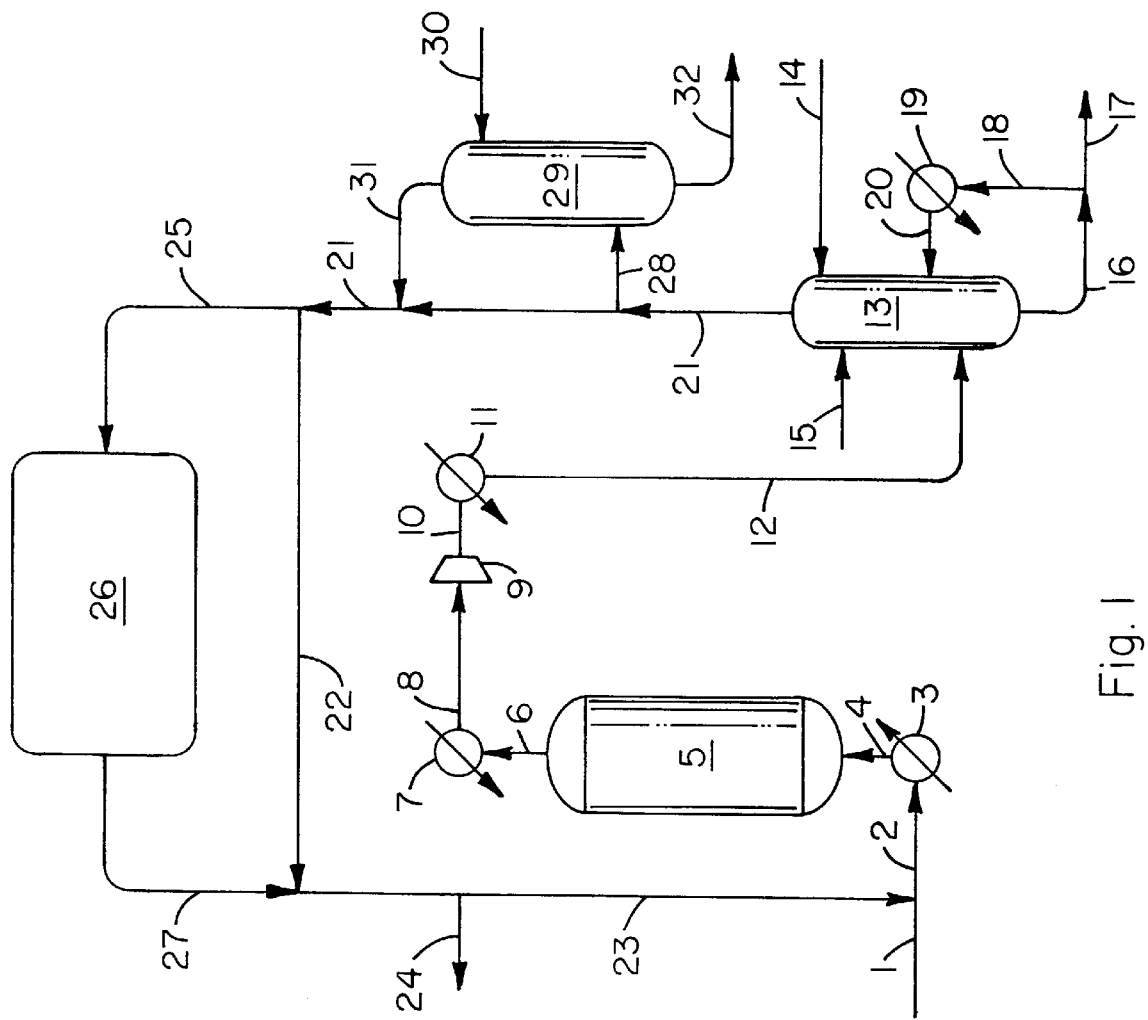
FIG. 1 is a process flow diagram illustrating an EpB production system which produces a butadiene epoxidation effluent recycle stream which may be used as the feed material for the carbon dioxide removal process of the present invention.

We have developed an efficient process for the removal of $CO_2$ from a butadiene epoxidation effluent recycle stream by contacting the stream with a solution of an alkanolamine. One embodiment of our invention, therefore, pertains to a process for the removal of carbon dioxide from a butadiene epoxidation effluent recycle gas stream comprising about 3 to 15 mole percent butadiene, about 8 to 25 mole percent oxygen, about 55 to 88 mole percent inert diluent gas and about 0.5 to 10 mole percent carbon dioxide which comprises feeding the gas stream to an absorption vessel wherein the gas stream is intimately contacted with a liquid solution of an alkanolamine at a pressure of about 0.1 to 1 MPa (14.5 to 145 psia) and a temperature of about 20 to 65° C. to obtain:

(1) a vapor effluent comprising butadiene, oxygen, inert diluent gas and about 0.005 to 0.5 mole percent carbon dioxide from the upper section of the absorption vessel; and (2) a liquid effluent comprising the alkanolamine solution and carbon dioxide-alkanolamine adduct from the lower section of the absorption vessel.

The CO2 removal process preferably is operated in conjunction with a wash operation wherein some or all of the gaseous effluent removed from the upper section of the $CO_2$ absorber normally is treated in a wash column to reduce the overall alkanolamine concentration in the gas recycled to the epoxidation zone. This wash operation represents a second step which comprises feeding vapor effluent (1) to a second absorption vessel wherein the gas stream is intimately contacted with a solvent at a pressure of about 0.1 to 1.1 MPa and a temperature of about 20 to 65° C. to obtain:

(3) a vapor effluent comprising butadiene, oxygen, inert diluent gas, about 0.005 to 0.5 mole percent carbon dioxide from the upper section of the absorption vessel, and less than 10 ppmv alkanolamine; and (4) a liquid effluent comprising solvent and absorbed alkanolamine from the lower section of the absorption vessel.

An optional third step of this preferred embodiment of the invention comprises recycling vapor effluent (3) to an epoxidation process wherein butadiene is contacted with an oxygen-containing gas in the presence of a silver catalyst.

Our novel process provides a means for the substantial removal of carbon dioxide from butadiene epoxidation recycle gas streams at low $CO_2$ pressure and high oxygen partial pressure in an efficient, safe and economical manner. Other embodiments of the present invention include the aforesaid $CO_2$ removal process operated in conjunction with an EpB production system and/or in conjunction with a process for the separation of $CO_2$ from the liquid effluent comprising the alkanolamine solution and carbon dioxide produced by the $CO_2$ removal process.

DETAILED DESCRIPTION OF THE INVENTION

The present invention may be used in combination with any epoxidation process wherein butadiene is contacted with an oxygen-containing gas in the presence of a catalyst and an inert gas to produce an epoxidation effluent comprising epoxybutene, butadiene, oxygen, an inert diluent, carbon dioxide and water. The silver-catalyzed, epoxidation processes described in U.S. Pat. Nos. 4,897,498, 4,950,773, 5,138,077 and 5,362,890 are typical of those which may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentration, e.g., up to about 18 mole percent, may be employed using methane as the inert diluent. When using butane as the inert diluent gas, relatively high oxygen concentrations, e.g., up to about 25 to 30 mole percent may be employed, depending on reactor pressure. The butadiene concentration typically is about 4 to 50 mole percent. The butadiene:oxygen mole ratio in the feed normally is maintained within the range of about 1:5 to 10:1. The inert gas usually constitutes about 25 to 85 mole percent of the total feed to the epoxidation zone. Normally, the feed also includes a small amount, e.g., 1 to 40 parts per million (ppm) of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 6 mole percent or greater, of impurities such as about 4 mole percent water. In accordance with the present invention, the carbon dioxide content of the feed to the epoxidation zone preferably is less than about 1000 ppmv, more preferably less than about 500 ppmv. Some argon may also be present in the feed. The amount of argon is controlled by purging a small amount of the recycle gas. Typically, the amount of argon is maintained at less than 10 percent, preferably less than 5 percent.

Although the reactor of the epoxidation zone may be operated at pressures ranging from 0.01 to 2.0 MPa, pressures in the range of about 0.1 to 1.0 MPa, preferably about 0.22 to 0.85 MPa, normally are used. The epoxidation feed typically is heated to about 175 to 225° C. in a pre-heater prior to entering the epoxidation reactor. The temperature of the epoxidation effluent is maintained at about 190 to 260° C., preferably about 210 to 245° C., by adjusting the temperatures of the reactor coolant, if employed, and/or pre-heater and/or the concentration of oxygen and/or the organic halide in the feed.

The silver catalysts described in U. S. Pat. No. 4,897,498 are examples of the epoxidation catalysts that may be used to convert butadiene to epoxybutene. The catalyst preferably is a supported, cesium-promoted, silver catalyst.

The gaseous epoxidation effluent typically comprises about 0.5 to 10 mole percent epoxybutene, about 4 to 50 mole percent butadiene, about 4 to 25 mole percent oxygen, about 0.5 to 10 $CO_2$ and about 25 to 85 mole percent inert gas. The effluent also contains a total of about 0.5 to 10 mole percent of water, acrolein, furan, vinylacetaldehyde, and crotonaldehyde, formed in the epoxidation zone. Unconsumed organic halide also is present in the epoxidation effluent. Typically the overall selectivity to epoxybutene is about 85–96%. As used herein, the percent conversion of butadiene is:

$$\frac{\text{Moles butadiene converted}}{\text{Moles butadiene fed}} \times 100$$

and the percent selectivity to 3,4-epoxy-1-butene is:

$$\frac{\text{Moles butadiene converted to 3,4-epoxy-1-butene}}{\text{Moles butadiene converted}} \times 100.$$

The epoxidation effluent is fed to a cooling/compression zone comprising one or more heat exchangers and one or more compressors wherein the effluent is pressurized to a pressure of about 0.3 to 2 MPa and cooled to a temperature of about 0 to 100° C. The cooling/compression zone may include a gas/liquid separator to remove any condensed liquids, e.g., water and/or butenediols (3-butene-1,2-diol and 2-butene-1,4-diol), from the pressurized and cooled effluent prior to feeding it to the absorption zone. The oxidation effluent which then is fed to the absorption zone usually contains about 1 to 5 mole percent water and formic acid, typically about 0.5 to 5 ppm (v/v) formic acid.

The EpB absorption zone comprises a columnar, pressure vessel containing trays or a packing material and is operated in the manner described in U.S. Pat. Nos. 5,117,012, 5,312, 931 and 5,756,779. When a mixture of butane and butadiene is used as the absorber solvent, the butane:butadiene mole ratio, normally is maintained in the range of about 20:1 to 1:2 with mole ratios of about 12:1 to 2:1 being preferred. A solution of epoxybutene in butadiene, or a mixture of butane and butadiene, is removed from the base of the absorption vessel and a vapor comprising butadiene, butane or other inert diluent, oxygen and carbon dioxide components of the epoxidation effluent is removed from the top of the vessel.

As stated hereinabove, the epoxidation effluent is intimately contacted with butadiene, or a mixture of liquid butane and butadiene, in the absorption zone at a pressure of about 0.2 to 1.0 MPa and a temperature of about 0 to 60° C. The absorption zone preferably is operated at pressures and temperatures of about 0.3 to 0.9 MPa and about 0 to 60° C. to minimize the reaction of the epoxybutene with the minor amounts of active hydrogen compounds present. In a preferred embodiment of my invention, the particular combination of pressure and temperature are selected to provide a predetermined concentration of butadiene, e.g., about 3 to 50, preferably about 7 to 20, mole percent, in the vapor effluent removed from the absorption vessel. The butadiene-containing vapor effluent thus obtained can be recycled, directly or indirectly, to the epoxidation zone and provide all of the butadiene reactant and diluent for the epoxidation reaction. When butane is employed as the inert diluent gas, the ratio of butane to butadiene in the absorber solvent also determines the concentration of these components in the gas effluent from the absorber. Thus, the butane:butadiene mole ratio in the absorber solvent is maintained to provide an absorber gas effluent containing about 4 to 50, preferably about 7 to 20, mole percent of butadiene, and about 25 to 85, preferably about 40 to 80, mole percent of butane. The mole percent composition of the vapor effluent from the absorber may be determined by applying both Dalton's law and Raoult's law to the components of the absorber.

The amount of the liquid butadiene or mixture of butane and butadiene mixture fed to the absorption vessel can vary substantially depending, for example, on the particular vessel, packing material and conditions employed and the feed rate and composition of the epoxidation effluent fed. Generally, the weight ratio of the absorber solvent feed to epoxidation effluent feed is in the range of about 0.1:1 to about 0.6:1. The temperature of the liquid butadiene or liquid mixture of butane and butadiene fed typically is in the range of about 0 to 60° C. A base compound also may be fed to the absorption vessel for the purpose of neutralizing any formic acid present and thus reducing the formation of butenediols. The addition of base may be carried out in the manner described in U.S. Pat. No. 5,756,779.

A liquid effluent (absorption underflow) comprising a solution of epoxybutene in butadiene, or mixture of butane and butadiene, is removed from the base of the absorption vessel and is fed to a butadiene or butane/butadiene recovery zone wherein EpB is separated from the absorption underflow. A portion, e.g., up to about 95 volume percent, of the underflow may be recycled to the absorption vessel. The recycle stream optionally may be cooled by means of a heat exchanger and returned to the lower section of the absorption vessel to control or regulate the temperature therein. As mentioned above, a basic compound or material may be added to this recycle stream. The concentration of epoxybutene in the absorption underflow stream may vary substantially, e.g., from about 2 to 40 weight percent based on the total weight of the stream. Normally, the epoxybutene concentration is in the range of about 5 to 15 weight percent (same basis). The underflow also contains minor amounts of water, diol and other materials, e.g., about 1 to 5 weight percent water and from about 0.01 to 2 weight percent diol.

The butadiene (or butane/butadiene) recovery zone comprises a distillation vessel, e.g., a column, a heat source at the base of the vessel, cooling means to condense vapor removed from the top of the vessel and a separator to separate water from the condensed liquid. The absorption column underflow may be fed to the mid-section of the recovery column to obtain (1) a gas effluent comprising butadiene or a mixture of butane and butadiene from the upper section of the column and (2) a liquid effluent comprising crude epoxybutene from the lower section of the column. The gas effluent contains a minor amount of water which may be removed from the epoxybutene production system by condensing the effluent to obtain a two-phase, liquid mixture and separating the aqueous phase from the butane/butadiene phase. Water and butadiene or butane form a constant boiling mixture (azeotrope) having a boiling point of approximately 43° C. at 0.48 MPa pressure. The water removal may be enhanced by recycling a portion, e.g., up to 95 weight percent, of the condensed butadiene or butane/butadiene phase to the upper section of the butane/butadiene recovery vessel. The water-depleted butadiene or butane/butadiene stream removed from the butane/butadiene recovery zone may be recycled, directly or indirectly, to the absorption zone along with fresh butane/butadiene. Fresh butadiene also must be added to make up for that consumed in the reactor zone. Make-up butadiene and butane may be added with the absorption column underflow to the butane/butadiene recovery zone. However, fresh butane/butadiene may be added at any point in the recycle loop and it is not necessary that the makeup butane/butadiene be added in the liquid mixture of butane and butadiene fed to the recovery column. The operation of the recovery column is described in U.S. Pat. Nos. 5,117,012, 5,312,931 and 5,756,779.

The vapor effluent removed from the EpB absorption vessel comprising butadiene, an inert diluent such as nitrogen, methane, butane(s), ethane, propane or pentane(s), oxygen and $CO_2$ is recycled, directly or indirectly, to the epoxidation zone. In accordance with the present invention, all or a part of the vapor from the EpB absorber is fed to a carbon dioxide removal zone wherein the carbon dioxide concentration of the gas is reduced to less than about 1 mole percent, preferably less than about 0.5 mole percent and most preferably to less than about 0.1 mole percent. The EpB absorber gas effluent typically comprises about 4 to 20 mole percent butadiene, about 60 to 88 mole percent inert gas, about 8 to 24 mole percent oxygen, and about 0.5 to 10 mole percent $CO_2$. The EpB absorber gas effluent also may contain minor amounts, e.g., a total of about 0.5 to 10 mole percent, of EpB, water, acrolein, furan, vinylacet-aldehyde, and crotonaldehyde. If the concentration of EpB in the EpB absorber gas effluent is significant, e.g., EpB concentrations of greater than about 0.1 mole percent, it may be advantageous to treat some or all of the EpB absorber gas effluent in a secondary EpB removal zone prior to feeding the gas to the carbon dioxide removal zone. One embodiment of the secondary EpB removal zone comprises a countercurrent absorber equipped with suitable packing or trays to provide intimate vapor-liquid contact wherein the EpB absorber gas effluent is contacted with an aqueous acidic solution to convert the EpB to higher boiling diols, predominately 1-butene-3,4-diol. The EpB absorber gas effluent is fed to the lower section of the absorber and the aqueous acid solution is fed to the upper section of an absorption tower. Temperature and pressure within the secondary EpB removal zone absorber are maintained in the range of about 0 to 65° C. and 0.1 to 1.1 MPa, preferably about 25 to 55° C. and 0.15 to 0.9 MPa. The EpB contained in the vapor feed reacts with the water in the aqueous acid feed via acid-catalyzed ring-opening to form primarily 1-butene-3,4-diol, along with some 2-butene-1,4-diol and oligomers thereof. The diols and oligomers are non-volatile and are removed from the EpB production system in the aqueous acid solution that is removed from the lower section of secondary EpB removal absorber. The gas treated in the secondary EpB removal absorber, substantially free of EpB, is removed from the upper section of the absorber. In this fashion, the EpB levels in the EpB absorber gas effluent may be reduced to less than 100 parts per million by volume (ppmv), preferably less than 50 ppmv, most preferably less than 10 ppmv.

The diol-laden, aqueous acid solution that is removed from the lower section of secondary EpB removal absorber may be recycled to the upper section of the secondary absorber. A fraction of the diol-containing solution must be purged to maintain the diol and oligomer content of the solution below about 10 weight percent, preferably below about 5 weight percent. Higher concentrations of diols and oligomer lead to reduced mass transfer efficiencies in the absorber and are more difficult to pump due to high viscosities. The flow rate of the aqueous acid solution should be sufficient to maintain good liquid wetting of packing or sufficient liquid depth on trays of the absorber comprising the EpB removal zone. Generally flow rates of at least 0.04 cubic meters per square meter of absorber-column cross-sectional area are sufficient.

Examples of acidic solutions which may be used in the secondary EpB removal zone components include aqueous solutions of non-volatile acids such as phosphoric acid, citric acid, sorbic acid, glycolic acid, and boric acid. Aqueous solutions of volatile acids, e.g., sulfuric, nitric, $C_1$–$C_6$ carboxylic acids, are not preferred because these acids or by-products therein, e.g., $SO_2$ and $NO_2$, may enter the secondary EpB removal absorber gas effluent and react irreversibly with the alkanolamine solution in carbon dioxide removal zone. Preferred concentrations of the acid component are 0.05 to 2 molar solutions, more preferably 0.05 to 1.0 molar solutions.

The carbon dioxide removal zone includes a $CO_2$ absorber comprising a columnar, pressure vessel containing trays or a packing material that facilitates intimate gas/liquid contact. Examples of suitable packing material include Koch-Sulzer packing, Pall rings, Berl saddles, and Penn State packing. The absorption vessel normally is provided with means, such as a disengaging space above the packing, to prevent or minimize entrainment of liquids in the gas stream removed from the upper section thereof. The vapor effluent from the EpB absorber vessel and/or EpB removal zone is fed to the lower section of the $CO_2$ absorber and a $CO_2$-lean alkanolamine-solvent solution is fed to the upper section of the $CO_2$ absorber. Carbon dioxide is absorbed by the conversion of the alkanolamine to the amine salt of a substituted carbamic acid ($CO_2$-alkanolamine adduct). The $CO_2$-rich $CO_2$-alkanolamine adduct salt is removed from the lower section of the $CO_2$ absorber and may be treated to regenerate and recovery the $CO_2$-free alkanolamine. The pressure and temperature within the $CO_2$ absorber normally are within the ranges of about 0.1 to 1.1 MPa, preferably 0.1 to 0.9 MPa, more preferably 0.2 to 0.85 MPa, and 20 to 65° C., preferably 30 to 55° C. A gaseous effluent removed from the upper section of the $CO_2$ absorber normally contains less than about 2000 ppmv, preferably less than 1000 ppmv, more preferably less than 500 ppmv (0.05 mole percent), carbon dioxide.

Suitable unsaturated or saturated alkanolamines for the present invention include primary and secondary amino alcohols containing a total of up to 10 carbon atoms and having a normal boiling point of less than about 250° C. Specific examples include primary amino alcohols such as monoethanolamine (MEA), 2-amino-2-methyl-1-propanol (AMP), 1-amino-3-buten-2-ol (AB-2-ol), 2-amino-3-buten-1-ol (AB-1-ol), 1-aminobutan-2-ol, 2-amino-butan-1-ol, 3-amino-3-methyl-2-pentanol, 2,3-dimethyl-3-amino-1-butanol, 2-amino-2-ethyl-1-butanol, 2-amino-2-methyl-3-pentanol, 2-amino-2-methyl-1-butanol, 2-amino-2-methyl-1-pentanol, 3-amino-3-methyl-1-butanol, 3-amino-3-methyl-2-butanol, 2-amino-2,3-dimethyl-1-butanol, and secondary amino alcohols such as diethanolamine (DEA), 2-(ethylamino)-ethanol (EAE), 2-(methylamino)-ethanol (MAE), 2-(propylamino)-ethanol, 2-(isopropylamino)-ethanol, 2-(butylamino)-ethanol, 1-(ethylamino)-ethanol, 1-(methylamino)-ethanol, 1-(propylamino)-ethanol, 1-(isopropylamino)-ethanol, 1-(butylamino)-ethanol, 1-methylamino-3-buten-2-ol, 2-methylamino-3-buten-1-ol, 1-ethylamino-3-buten-2-ol, 2-ethylamino-3-buten-1-ol, 1-propylamino-3-buten-2-ol, 2-propylamino-3-buten-1-ol, 1-butylamino-3-buten-2-ol, 2-butylamino-3-buten-1-ol. Moreover, we have found that the reaction products of EpB and the primary amines, e.g., secondary amines formed in the carbon dioxide removal zone, function as effectively for our invention as the original primary amines. Thus, for example the reaction product of EpB with MEA, the secondary amine 1-(2-hydroxyethylamino)-3-buten-2-ol (EBA), functions as an effective carbon dioxide absorbent in our invention. Mixtures comprising two or more of the above alkanolamines are also effective for our invention. The most preferred alkanolamines comprise MEA, AMP, EAE, AB-1-ol, AB-2-ol, mixtures of any two or more thereof, and mixtures of any of these amines with their EpB-primary amine reaction products, e.g., a mixture of MEA and EBA. Generally the molar ratio of the EPB-primary amine reaction product to the primary amine (e.g., EBA:MEA ratio) should be kept between 0 to 3:1, preferably 0 to 1.5:1, most preferably 0 to 0.5:1 ratio. Tertiary amines and the EpB-secondary amine reaction products, e.g., (2-hydroxyethyl)-bis-(2-hydroxy-3-butenyl)amine (EDBA), are not preferred for our invention because of the low $CO_2$ capacity and high partial pressures of $CO_2$ above such solutions of alkanolamines at the low absorption pressures utilized in the process of our invention.

The alkanolamine or mixtures of alkanolamines are used as a solution in water, an alkanol, a glycol or a mixture of any two or more thereof. The alkanols may contain up to about 8 carbon atoms and the glycols may contain 2 to 4 carbon atoms. Examples of useful alkanols and glycols are butanol, pentanol, hexanol, ethylene glycol, propylene glycol, butylene glycol, 1-butene-3,4-diol, and 2-butene-1,4-diol. Aqueous solutions are preferred. The preferred concentration range of alkanolamine or mixture of alkanolamines in water is 7 to 65 weight percent alkanolamine in water. For MEA and MEANEBA solutions the concentration is preferably 10 to 45 weight percent in water, more preferably 12 to 35 weight percent in water. For AMP the preferred solution concentration is 15 to 40 weight percent in water. The alkanolamine solution flowrate is set to give a carbon dioxide:alkanolamine molar ratio within the $CO_2$ absorber of 0.25 to 1.0 moles carbon dioxide:mole alkanolamine. Preferably for MEA and MEA/EBA solutions the carbon dioxide:alkanolamine molar ratio is 0.25 to 0.65, more preferably 0.35 to 0.45. The preferred carbon dioxide:alkanolamine mole ratio for AMP solutions is 0.35 to 0.7.

Optionally, a corrosion and degradation inhibitor may be added to the alkanolamine solution. Any suitable copper or vanadium-based inhibitor known in art to be compatible with alkanolamines may be used.

As explained in Lees, F. P., "Loss Prevention in the Process Industries, Volume 1," 485–86 (1980) and Coffee, R. D., Loss Prevention 13, 74–80, (1980), a flammable gas, e.g., methane, butane, and other alkane hydrocarbons, burns in oxidizing environments only over a limited composition range. The limits of flammability (often called the explosive limits) are the concentration extremes at which a mixture of a flammable gas and an oxidant can continue to burn once a flame is ignited by an external energy source such as a spark. These flammability extremes are a function of temperature, pressure, and composition. The explosive limit is usually expressed as volume or mole percent flammable gas in a mixture of oxidant (usually oxygen), inert, and flammable gas. The smaller value is the lower (lean) limit and the larger value is the upper (rich) limit. For example n-butane-oxygen mixtures will propagate flames for n-butane concentrations between 1.8 and 49 mole percent n-butane and n-butane-air mixtures between 1.83 and 8.4 mole percent n-butane, at 25° C. and atmospheric pressure. In general, the lower explosive limit (LEL) decreases, and the upper explosive limit (UEL) increases as temperature and pressure increase, and amount of inert decreases. Generally, increases in pressure have a larger effect than the increases in temperature. The explosive limits of flammable gas mixtures, e.g., n-butane and 1,3-butadiene, can be estimated by the well-known LeChatlier's rule.

The maximum safe oxygen content of the epoxidation recycle gas is dictated by the upper flammability limit of the gas mixture at the outlet of the recycle compressor and the temperature, pressure, and composition conditions of streams recycle stream and the feed streams to the EpB and $CO_2$ absorber, depending on the chosen compression option. For example, with a mixture of butadiene and n-butane diluent gas and under conditions where potassium carbonate is clearly the favored method for carbon dioxide removal from butadiene epoxidation recycle gases (an example counter to our invention), the compressor outlet pressure should be above at least about 1.4 MPa (with 1–2 mole percent carbon dioxide). The maximum safe oxygen content at 1.4 MPa and a reasonable compressor outlet temperature of 85° C. is only 16 mole percent oxygen. Alternatively, according to our invention, alkanolamine solutions can be used to absorb substantially all of the carbon dioxide from epoxidation recycle loop gases at pressures an order of magnitude lower, i.e., as low as 0.14 MPa. The maximum safe oxygen content at 0.14 MPa and a reasonable compressor outlet temperature of 85° C. is 40 mole percent oxygen. Thus, our invention allows higher oxygen levels to be used safely, while still providing high carbon dioxide removal efficiencies.

The outlet pressure for the $CO_2$ absorber feed compressor may be in the range of about 0.2 to 1.1 MPa, preferably 0.2 to 0.95 MPa, more preferably 0.22 to 0.85 MPa. Such an outlet pressure optimizes carbon dioxide partial pressure requirements for good absorption with an alkanolamine solution, the need for high oxygen levels for improved reactor performance, and process safety tradeoffs.

The gaseous effluent removed from the upper section of the $CO_2$ absorber may be recycled to the epoxidation zone and provides both the butadiene reactant and the diluent gas, e.g., n-butane, for the epoxidation reaction. Since oxygen is consumed in the epoxidation zone, the oxygen content of the butadiene-containing recycle effluent gas obtained from the carbon dioxide removal zone is supplemented by an oxygen feed prior to feeding the gas to the epoxidation zone.

Normally, an organic halide (discussed hereinabove) also is added to the effluent gas. Normally, a small amount of the recycle stream is purged from the production system to remove argon, an impurity present in the oxygen feed to the epoxidation zone.

We have discovered that low levels, e.g., concentrations as low as about 15.0 ppmv, of alkanolamine in the gaseous effluent from the $CO_2$ absorber reversibly poison the silver-based epoxidation catalyst. Although catalytst activity usually returns upon removal of the alkanolamine from the feed to the reactor, it is desirable to maintain the alkanolamine concentration in the gas which is recycled to the epoxidation zone at less than 10.0 ppmv, preferably less than 5.0 ppmv, more preferably less than 1.0 ppmv, in order to maintain a continuous, high level of catalyst productivity. Although the alkanolamines are relatively non-volatile, the concentration of alkanolamine(s) in the gaseous effluent from the $CO_2$ absorber may be 2000 ppmv or greater, typically from about 20 to 600 ppmv. Therefore, a fraction, typically at least 50%, or all of the gaseous effluent removed from the upper section of the $CO_2$ absorber normally is treated in a wash column to reduce the overall alkanolamine concentration in the gas recycled to the epoxidation zone. The wash column reduces alkanolamine concentration to levels which permit the maintenance of high epoxidation catalyst activity, e.g., alkanolamine concentrations below 10.0 ppmv, preferably less than 5.0 ppmv, more preferably less than 1.0 ppmv.

The $CO_2$ absorber gas effluent is fed to the lower section and solvent is fed to the upper section of the wash column that contains a suitable packing material or trays to provide intimate vapor/liquid. In this fashion, the alkanolamine content of the $CO_2$ absorber gas effluent can be reduced to less than 10.0 ppmv, preferably less than 5.0 ppmv, more preferably less than 1.0 ppmv. The temperature and pressure within the wash column typically are maintained within the ranges of about 20 to 65° C. and 0.1 to 1.1 MPa, preferably within the ranges of about 25 to 55° C. and 0.2 to 0.9 MPa.

Suitable solvents for use in the wash column include water, alkanols, glycols or a mixture of any two or more thereof. The alkanols may contain up to about 8 carbon atoms and the glycols may contain 2 to 4 carbon atoms. Examples of useful alkanols and glycols are butanol, pentanol, hexanol, ethylene glycol, propylene glycol, butylene glycol, 1-butene-3,4-diol, and 2-butene-1,4-diol. Water is the preferred solvent. A liquid stream comprising solvent and absorbed alkanolamine is removed from the lower section of the water wash column and can be discarded as waste or, more preferably, combined with the liquid underflow from the $CO_2$ absorber for later recovery of alkanolamine. A gas effluent is removed from the upper section of the water wash section and may be recycled to the epoxidation zone as described above.

The combination of the above-described carbon dioxide removal process with the wash (alkanolamine removal) column constitutes a second and preferred embodiment of the present invention. This embodiment involves a process for the removal of carbon dioxide from a butadiene epoxidation effluent recycle gas stream about 3 to 15 mole percent butadiene, about 8 to 25 mole percent oxygen, about 55 to 88 mole percent inert diluent gas and about 0.5 to 10 mole percent carbon dioxide which comprises the steps of:

(I) feeding the gas stream to a first absorption vessel wherein the gas stream is intimately contacted with a liquid solution of an alkanolamine at a pressure of about 0.1 to 1 MPa (14.5 to 145 psia) and a temperature of about 20 to 65° C. to obtain:
  (i) a vapor effluent comprising butadiene, oxygen, inert diluent gas, about 0.005 to 0.5 mole percent carbon dioxide from the upper section of the absorption vessel, and about 20 to 2000 ppmv alkanolamine; and
  (ii) a liquid effluent comprising the alkanolamine solution and carbon dioxide-alkanolamine adduct from the lower section of the first absorption vessel; and
(II) feeding vapor effluent (i) to a second absorption vessel wherein the gas stream is intimately contacted with a solvent at a pressure of about 0.1 to 1.1 MPa and a temperature of about 20 to 65° C. to obtain:
  (iii) a vapor effluent comprising butadiene, oxygen, inert diluent gas, about 0.005 to 0.5 mole percent carbon dioxide from the upper section of the absorption vessel, and less than 10 ppmv alkanolamine; and
  (iv) a liquid effluent comprising solvent and absorbed alkanolamine from the lower section of the absorption vessel.

An optional third step of this preferred embodiment of the invention comprises recycling vapor effluent (iii) to an epoxidation process wherein butadiene is contacted with an oxygen-containing gas in the presence of a silver catalyst.

The liquid effluent from the $CO_2$ absorber and, optionally, the liquid effluent from the wash column may be subjected to further processing in an alkanolamine reclamation zone to remove $CO_2$ and recover alkanolamine from the effluents by decomposing alkanolamine-$CO_2$ salts. In the alkanolamine reclamation zone, the aforesaid liquid effluents optionally are degassed at elevated temperature, e.g., at about 65 to 90° C., and at pressures from 0.1 MPa and 0.35 MPa to promote the evolution of gases such as oxygen (which promotes degradation of the alkanolamine in the salt decomposition column), nitrogen and argon. The degassed liquid then is fed to a salt decomposition column comprising a packed or trayed column wherein the alkanolamine-$CO_2$ salt or salts are decomposed at elevated temperature into free alkanolamine and carbon dioxide. The heat required for this endothermic reaction is supplied by direct contact heating with steam or other suitable heating media or more preferably by means of a reboiler.

A liquid underflow is withdrawn from the bottom sump of the salt decomposition column and a portion is fed to a reboiler to provide boil-up and heat for decomposition of the alkanolamine-$CO_2$ salt. The temperature within the reboiler is maintained at about 90 to 165° C., preferably about 100 to 125° C., by steam or other suitable heating media. The temperature and heat input to the reboiler is adjusted to maintain the $CO_2$/alkanolamine molar ratio in the liquid underflow stream at not more than 0.2, preferably not more than 0. 15, more preferably not more than 0.10. Vaporized materials, e.g., water, alkanolamine, and gases, e.g., carbon dioxide, oxygen, ammonia, nitrogen, argon, pass out of the top of the salt decomposition column and are partially condensed. Noncondensables, e.g., carbon dioxide, oxygen, ammonia, nitrogen, argon, and saturation levels of water and alkanolamine are removed from the reclamation zone. Reflux is provided to maintain low levels of alkanolamine in the overhead. Excess water and traces of alkanolamine may be removed from the reflux system and discarded.

A fraction of the column underflow (regenerated alkanolamine solution) is purged to control the build-up of heat-stable salts, e.g., alkanol-amine-oxalates, -acetates, -formates, and the like, which are formed by the oxidative degradation of alkanolamines. The purge rate typically is between about 0.05 to 0.5 weight percent, preferably 0.1 to 0.3 weight percent of the underflow stream. As an alternative to, or in conjunction with, this purge, a fraction, i.e., 0.05 to 10 weight percent, of the regenerated alkanolamine solution may be passed, either in a batch mode or continuous mode, to a secondary salt removal unit comprising a reboiler type heat exchanger heated by steam or other suitable heating media. The secondary salt removal unit serves to increase the recovery of valuable alkanolamines and reduce the losses to the purge stream. The temperature within the secondary salt removal unit is maintained in the range of about 125 to 225° C. and a pressure of less than 0.2 MPa. Within the secondary salt removal unit, the lighter (lower boiling) alkanolamine components are vaporized and recovered for recycle to the carbon dioxide removal zone. Thus, when the alkanolamine is monoethanolamine, essentially all of the non-volatile heat-stable salts, e.g., alkanolamine-oxalates, -acetates, -formates, and the high-boiling EDBA and some EBA are removed and water, MEA, and a fraction of the EBA are recovered for reuse in the carbon dioxide removal zone.

The combination of above-described carbon dioxide removal process with the alkanolamine reclamation process represents a third embodiment of our invention. This embodiment involves the process for the removal of carbon dioxide from a butadiene epoxidation effluent recycle gas stream comprising about 5 to 15 mole percent butadiene, about 8 to 25 mole percent oxygen, about 55 to 88 mole percent inert diluent gas and about 0.5 to 10 mole percent carbon dioxide which comprises the steps of:

(I) feeding the gas stream to an absorption vessel wherein the gas stream is intimately contacted with a liquid solution of an alkanolamine at a pressure of about 0.1 to 1.0 MPa and a temperature of about 5 to 50° C. to obtain:

(i) a vapor effluent comprising butadiene, oxygen, inert diluent gas and about 0.005 to 0.5 mole percent carbon dioxide from the upper section of the absorption vessel; and (ii) a liquid effluent comprising the alkanolamine solution and carbon dioxide-alkanolamine adduct from the lower section of the absorption vessel; and (II) subjecting liquid effluent (ii) to an alkanolamine reclamation process which comprises feeding liquid efficient (ii) to the lower section of a column wherein the liquid is heated at a temperature of about 90 to 165° C. to obtain:

(iii) a vapor effluent comprising carbon dioxide from the upper section of the column; and (iv) a liquid effluent comprising the alkanolamine solution substantially free of carbon dioxide-alkanolamine adduct from the lower section of the column.

The alkanolamine reclamation process preferably includes an initial degassing step which comprises heating the liquid effluent (ii) at a temperature of about 65 to 90° C. and at a pressure of from 0.1 MPa and 0.35 MPa, preferably at ambient pressure, to remove dissolved gases from the liquid. As described herein, the feed to the alkanolamine reclamation process can include the liquid effluent obtained from the solvent wash column.

The bulk of the regenerated alkanolamine solution is cooled and recycled to the carbon dioxide removal zone. Fresh alkanolamine solution is added to maintain the inventory of alkanolamine in the regenerated alkanolamine recycle stream. Sufficient fresh alkanolamine is added to maintain an alkanolamine concentration between 5 and 65 weight percent in the stream recycled to the carbon dioxide removal zone. The recycle stream typically is cooled to 25 to 65° C., preferably less than 50° C., more preferably less than 45° C.

Some or all, e.g., 1.0 to 100 weight percent, preferably 1 to 25 weight percent, may be fed to an adsorption-filtration zone wherein solid particles, high molecular weight acid oxidative by-products, and ionic species, e.g., iron, that may degrade the performance of the alkanolamine or promote corrosion of equipment are removed. The adsorption-filtration may contain any or all of the following items: a mechanical filter, activated carbon bed, and ion exchange bed. The preferred embodiment comprises a mechanical filter followed by an activated carbon bed. The filter media in he mechanical filter should have a pore size of 10–75 microns.

The absorbers employed in the practice of the present invention typically are provided with any gas/liquid contacting device known in the art suitable for conventional absorption practice. The gas/liquid contacting equipment in these absorption zones may include but are not limited to cross-flow sieve, valve, or bubble cap trays, structured packings such as the materials sold under the tradenames Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. *Distillation Design,*McGraw-Hill, New York (1992)

Referring to accompanying FIG. 1, a mixture comprising butane (an example of diluent gas which may be used), butadiene, oxygen, and an organic halide is fed by conduit 2 to heat exchanger 3 wherein the mixture is preheated to a temperature of about 175 to 225° C. and then is fed via conduit 4 to epoxidation reactor 5. The epoxidation reactor may contain a plurality of steel tubes packed with a silver catalyst such as a cesium-promoted, supported, silver catalyst. The gas feed passes through the catalyst-containing steel tubes wherein butadiene is selectively oxidized to epoxybutene and exits the epoxidation reactor through conduit 6. A heat exchange fluid is passed over the exterior of the reactor tubes to remove the heat of reaction. The temperature and pressure within conduit 6 typically is about 0.1 to 0.9 MPa and 180 to 245° C.

The epoxidation effluent is fed to heat exchangers 7 and 11 and compressor 9 by conduits 6, 8 and 10 wherein the temperature of the effluent stream is reduced to about 0 to 100° C. and the pressure is increased to about 0.2 to 1.1 MPa. The cooled and pressurized effluent is transported by conduit 12 to absorber 13.

A mixture of liquid butane and butadiene is fed through conduit 14 to the upper section of absorber 13 which contains a suitable packing material to provide intimate contact between the effluent fed by line 12 and liquid butane/butadiene mixture fed by line 14. An 0.5 to 10 weight percent aqueous potassium bicarbonate may be fed absorber 13 by line 15 to neutralize any acidic compounds, e.g., formic acid, present in the feed to the absorber. The pressure and temperature within absorber 13 are within the ranges of about 0.1 to 1.1 MPa and −5 to 65° C., provided that the combination of pressure and temperature maintains a liquid phase within the absorber. The conditions of pressure and temperature also are controlled to provide a predetermined concentration of both butane and butadiene in the gaseous effluent removed from the top of the absorber.

A liquid effluent comprising a solution of epoxybutene in butane/butadiene is removed from the base of absorber 13 and transported via conduits 16 and 17 to an EpB refining zone (not shown) wherein the EpB and the butane/butadiene absorption solvent water are separated and the crude EpB may be further refined, if necessary, to increase the purity of the EpB, e.g., to 99+%. A portion, e.g., up to about 95 weight percent, of the liquid effluent stream may be recycled through conduits 18, heat exchanger 19 and conduit 20 to absorber 13. This recycle stream functions to provide additional cooling of the contents of the absorber.

A vapor effluent comprising butadiene, butane, and oxygen is removed from absorber 13 via conduit 21 and, if not previously pressurized, is pressurized to about 0.2 to 1.1 MPa and then is fed via conduit 25 to carbon dioxide removal zone 26. Normally, the butadiene content of the vapor effluent is within the range of about 4 to 50, preferably about 7 to 20 mole percent. Additionally, butane usually constitutes about 25 to 85 mole percent of the total feed to the epoxidation zone. The effluent from the carbon dioxide removal zone is recycled to epoxidation reactor 5 via lines 27, 23, 2, and 4 and preheater 3 and provides both the butadiene reactant and inert gas, e.g., butane, for the epoxidation reaction. The butane- (or butane/butadiene-) containing vapor effluent is conveyed to epoxidation reactor 5 by conduits 27, 23, 2 and 4 and preheater 3 and provides both the butadiene reactant and the inert gas, e.g., butane, for the epoxidation reaction. Oxygen is combined via conduit 1 with the effluent of line 23 to bring the concentration of oxygen in the reactor feed to about 5 to 30 mole percent. All or part of the vapor effluent removed from epoxybutene absorber 13 via line 21 may be transported, intermittently or continusously, directly by conduits 22, 23, 2 and 4 and preheater 3 to epoxidation reactor 5. A small purge via line 24 normally is required to remove argon, an impurity present in the oxygen feed to the epoxidation zone.

Optionally, some or all of the vapor effluent of stream 21 may be conveyed via conduit 28 to secondary EpB removal zone 29 which comprises a countercurrent absorber wherein the vapor in conduit 21 is fed to the lower section of the absorber and countercurrently contacted with an aqueous, acidic solution, fed via conduit 30 to the upper section of absorption tower 29 equipped with suitable packing or trays for intimate vapor-liquid contacting. EpB present in vapor stream 21 reacts with the water in stream 30 via acid-catalyzed, ring-opening to form predominately 1-butene-3,4-diol, along with some 2-butene-1,4-diol and oligomers thereof. EpB levels in conduit 21 may be reduced by EpB removal zone to less than 100 parts per million by volume (ppmv), preferably less than 50 ppmv, more preferably less than 10 ppmv. Temperature and pressure within absorber 29 are maintained in the range of about 0 to 65° C. and 0.1 to 1.1 MPa, preferably about 25 to 55° C. and 0.15 to 0.85 MPa. The diols and oligomers are non-volatile and remain in the aqueous, acidic, liquid phase which is removed from absorber 29 by conduit 32. The diol-containing stream 32 may be recycled via conduit 30 to absorber 29 although a fraction thereof must be purged to maintain the diol and oligomer content of the stream below about 10 weight percent, preferably below about 5 weight percent. An EpB-lean vapor effluent is removed from absorber 29 by means of conduit 31 and transported to the carbon dioxide removal zone 26 via conduit 21 and 25.

Absorption zones 13 and 29 may be combined within a single column shell if desired. The upper section 29 may be separated from the lower section 13 by any appropriate partitioning device known in the art such as a chimney tray with a total liquid draw-off sump.

Figure 2:
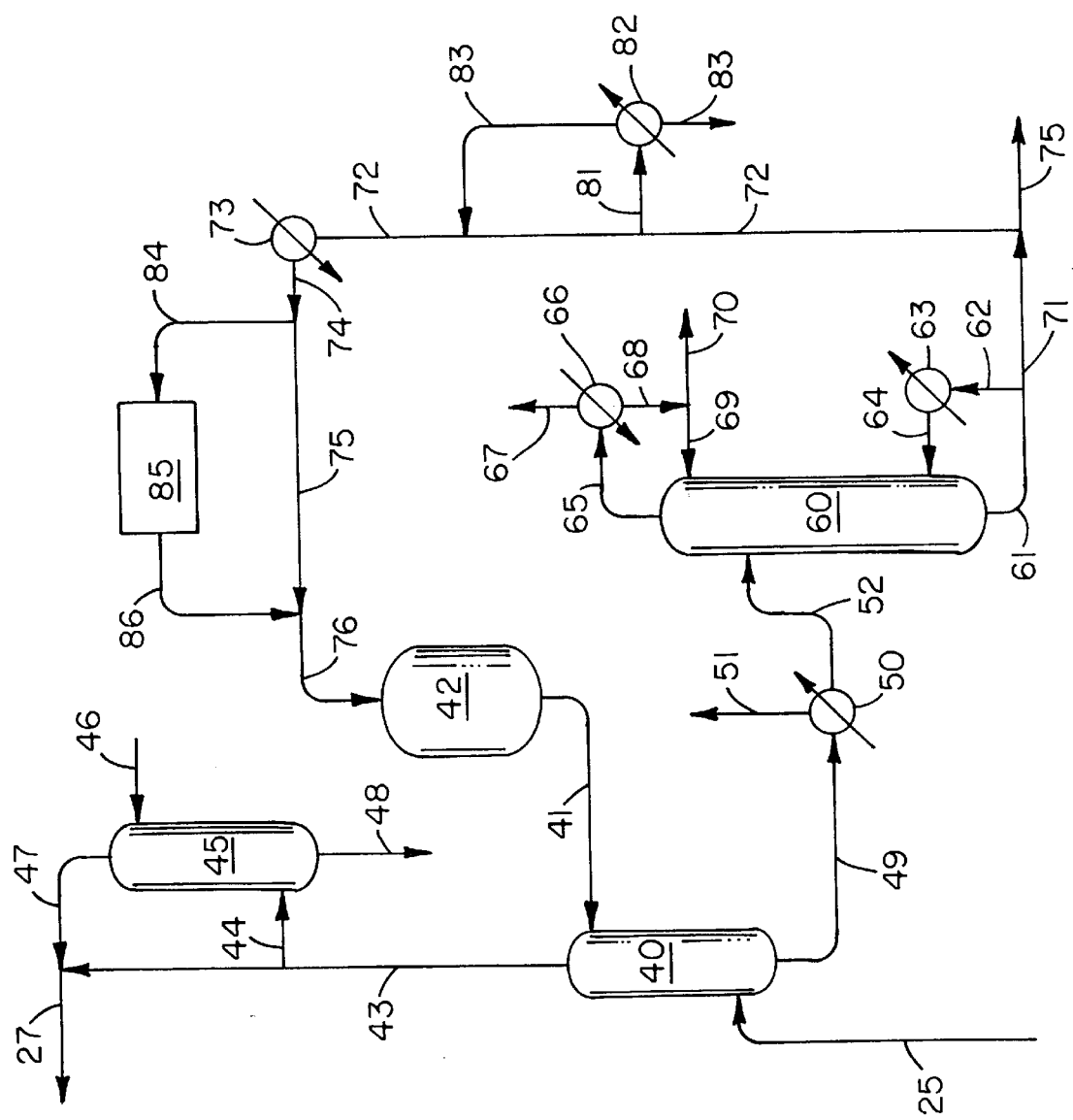
FIG. 2 is a process flow diagram illustrating a carbon dioxide removal system embodying the principles of the processes of the present invention. While the present invention is susceptible to embodiment in various forms, there is shown in the Figures and hereinafter described in detail preferred embodiments of the invention. However, the present disclosure is to be considered as an exemplification of the invention without limitation to the specific embodiments illustrated.

Referring to FIG. 2 which illustrates one embodiment for the practice of the present invention, vapor effluent contained in conduit 25 from absorber 13 (and, optionally, secondary EpB removal absorber 29) is fed to a carbon dioxide removal zone comprising $CO_2$ absorber 40, wash column 45 and salt decomposition column 60. The vapor feed of conduit 25 may pass directly to $CO_2$ absorber 40 without previous compression if the pressure in conduit 25 is sufficient to overcome the pressure drop across $CO_2$ absorber 40 and wash column 45. The vapor effluent is fed by conduit 25 to the lower section of absorber 40 that contains an appropriate packing material or trays. An alkanolamine solution ($CO_2$-lean) is fed via conduit 41 to the upper section of absorber 40 from alkanolamine solution feed tank 42. $CO_2$ is absorbed by reacting with the alkanolamine to form an amine salt of a substituted carbamic acid. The liquid solution of $CO_2$-rich alkanolamine/$CO_2$ salt is removed via conduit 49 from the lower section of absorber 40 for regeneration. The pressure and temperature within $CO_2$ absorber 40 are within the ranges of about 0.1 to 1.1 MPa, preferably 0. 1 to 0.9 MPa, more preferably 0.2 to 0.85 MPa, and 20 to 65° C., preferably 30 to 55° C. A vapor effluent, comprising less than about 2000 ppmv $CO_2$, preferably less than 1000 ppmv, more preferably less than 500 ppmv (0.05 mole percent) of carbon dioxide, is removed from the upper section of absorber 40 via conduit 43. This vapor effluent may be returned by means of conduits 43, 27, (with reference to FIG. 1) 23, 2 and 4 and preheater 3 to epoxidation reactor 5

A fraction, typically at least 50%, or all of the absorber 40 vapor effluent is sent via conduits 43 and 44 to the lower section of wash column 45 to reduce the level of vaporized alkanolamine present in stream 43 to less than 10.0 ppmv, preferably less than 5.0 ppmv, more preferably less than 1.0 ppmv. A liquid comprising water is fed via conduit 46 to the upper section of column 45 and contacts the rising vapor feed in column 45 which contains a suitable packing material or trays to provide intimate vapor/liquid. A vapor effluent depleted in alkanolamine is removed from the upper section column 45 via conduit 47 and is fed to line 27 for recycle to the epoxidation zone as described hereinabove. A liquid effluent comprising water and absorbed alkanolamine is removed from the lower section of column 45 through conduit 48. This liquid can be discarded or, advantageously, it may be sent via conduit 48 to conduit 49 for recovery of alkanolamine. The pressure and temperature within wash column 45 are within the ranges of about 0.1 to 1.1 MPa, preferably 0.1 to 0.9 MPa, more preferably 0.2 to 0.85 MPa, and 20 to 65° C., preferably 30 to 55° C. Absorption zone 40 and wash zone 45 may be combined within a single column in the manner described above for absorbers 13 and 29.

The $CO_2$-containing, alkanolamine salt stream 49 (and optionally the effluent 48 from water wash column 40) are preheated and the pressure may be reduced in heat exchanger 50. It is preferred that the pressure within conduit 49 be adjusted, if necessary, to approximately atmospheric pressure. Heating the solution contained in conduit 49 at approximately ambient pressure results in the evolution of gases (degassing of the liquid) such as oxygen which can cause degradation of the alkanolamine present degradation in salt decomposition column 60. Evolved gases, e.g., oxygen, nitrogen, argon, are removed via conduit 51. The degassed liquid is conveyed via conduit 52 to the upper section of column 60 which contains packing material or trays wherein the alkanolamine-$CO_2$ salt is decomposed at elevated temperature into free alkanolamine and $CO_2$. according to the embodiment shown in FIG. 2, the heat required for this endothermic decomposition reaction is provided by reboiler 63. Liquid withdrawn from the lower section or bottom sump of column 60 is passed via conduits 61 and 62 to reboiler 63 wherein the temperature is adjusted to maintain the $CO_2$/alkanolamine molar ratio in stream 61

(regenerated alkanolamine solution) at not more than 0.2:1. Liquid vaporized in reboiler 63 is returned via conduit 64 to the lower section of column 60 to provide boil-up and heat for decomposition of the alkanolamine-$CO_2$ salt. A vapor stream comprising alkanolamine solvent, alkanolamine, and gases such as $CO_2$, oxygen, ammonia, nitrogen and argon are removed from column 60 through conduit 65 and fed to heat exchanger 66 wherein the components of stream 65 are partially condensed. Noncondensable components such as $CO_2$, oxygen, ammonia, nitrogen, argon, and saturation levels of water and alkanolamine exit the alkanolamine reclamation zone via conduit 67. Reflux is provided via conduits 68 and 69 to maintain low levels of alkanolamine in the overhead vapor 65. Excess water and traces of alkanolamine are discarded from the alkanolamine reclamation zone via conduit 70.

A fraction of the stream 61 liquid (regenerated alkanolamine solution) normally is purged from the alkanolamine reclamation zone via conduits 71 and 75 to control the build-up of heat-stable salts formed by the oxidative degradation of alkanolamines. The purge rate typically is between about 0.05 to 0.5 weight percent, preferably 0.1 to 0.3 weight percent of the underflow stream. The bulk of the regenerated alkanolamine solution is conveyed via conduits 61, 71 and 72 to heat exchanger 73 wherein the solution is cooled to 25 to 65° C., preferably less than 50° C., more preferably less than 45° C. If desired for energy savings, stream 49 ay interchange heat duty with stream 72. For example, heat exchanger 73 may be the same piece of equipment as heat exchanger 50, i.e., stream 49 serves as the heat exchange medium for stream 72.

A portion, e.g., 0.05 to 10 weight percent, of the regenerated alkanolamine solution of conduit 72 may be passed via conduit 81, either in a batch mode or continuous mode, to heat exchanger 82 which serves to increase the recovery of valuable alkanolamines and reduce the losses to purge stream 75. Heat is supplied by steam or other suitable heating media to heat the liquid feed from conduit 81 to a temperature of about 125 to 225° C. at a pressure of less than 0.2 MPa. Within heat exchanger 82, the lighter (lower boiling) alkanolamine component or components of stream 81 are vaporized and recovered in conduit 83 and conveyed to line 72 as shown or, alternatively, to heat exchanger 73. High boiling and non-volatile components such as alkanolamine-oxalates, -acetates, -formates are removed from the alkanolamine reclamation zone by line 83. For example, in the embodiment of our invention in which the alkanolamine is monoethanolamine, substantially all of the non-volatile heat-stable salts, e.g., alkanolamine-oxalates, -acetates, -formates, and the high-boiling EDBA and some EBA are removed via conduit 83. The water, MEA, and a fraction of the EBA are recovered for reuse in stream 83. Fresh alkanolamine solution may be added to conduit 72 to maintain the inventory of alkanolamine in the alkanolamine recycle system. Sufficient fresh alkanolamine is added to maintain a total primary and secondary alkanolamine concentration between 5 and 65 weight percent in stream 74. The cooled stream 74 from the outlet of exchanger 73 is conveyed via conduit 74 to the feed tank 42 and then to carbon dioxide absorber 40.

Some or all of stream 74, e.g., about 1.0 to 100 weight percent, preferably 1 to 25 weight percent, is conveyed via conduit 84 to adsorption-filtration zone 85 wherein solid particles, high molecular weight acid oxidative by-products, and ionic species, e.g., iron, that may degrade the performance of the alkanolamine or promote corrosion of equipment are removed. Adsorption-filtration zone 85 may contain a mechanical filter, an activated carbon bed, and/or an ion exchange bed. The preferred embodiment comprises a mechanical filter followed by an activated carbon bed. The filter media in the mechanical filter should have a pore size of 10–75 microns. Examples of suitable ion exchange resins include those sold under the tradenames DOWEX™ 1, DOWEX™ 2, DOWEX™ MSA-1. A suitable activated carbon is for example Calgon™ F-300.

The processes provided by the present invention are further illustrated by the following examples.

EXAMPLE 1

This example illustrates the operation of an integrated epoxidation recycle gas process with an alkanolamine solution for carbon dioxide absorption as depicted in FIGS. 1 and 2. Recycle gas having an average composition comprising about 18 mole percent oxygen, 9 mole percent 1,3-butadiene, 60 mole percent n-butane, 2–4 ppmv 2-chlorobutane, and less than 100 ppmv carbon dioxide was fed via conduit 2 at a rate of 175 standard liters per minute to heat exchanger 3 wherein the feed mixture was preheated to about 199° C. at a pressure of about 0.28 MPa (40 psia). The gas mixture was fed via line 4 to reactor 5 comprising a stainless steel tube, 7.62 meters tall, 41 mm inside diameter, packed with 1.2 meters of Denstone ceramic packing on top of 8.4 liters of silver/cesium/alumina catalyst rings. Average maximum temperature in epoxidation reactor 5 was maintained at 214° C.

The epoxidation catalyst employed comprised an alumina support in the form of 6 mm outside diameter rings having deposited thereon 12 weight percent silver and 700 parts per million by weight (ppmv) cesium. The catalyst was prepared according to known procedures by impregnating the support material with solutions of a silver amine salt and cesium chloride followed by a thermal decomposition/reduction treatment in the presence of an oxygen-containing gas to convert the silver salt to silver metal.

A vapor effluent was removed from reactor 5 via line 6, cooled in heat exchanger 7 and fed through line 8 to compressor 9 wherein the epoxidation effluent was compressed to about 0.55 MPa (80 psia). The compressed gas was fed via line 12 to the lower section of EpB absorber 13 comprising a stainless steel column, 102 mm in diameter, packed with about 1.8 meters of 9.5 mm stainless steel Penn State packing. A mixture of n-butane and butadiene was fed to the upper section of the absorber via conduit 14. The absorber operated at about 0.52 MPa (75 psia) outlet pressure and an average temperature of about 40° C. A vapor effluent removed from the EpB absorber by conduit 21 averaged about 500 ppmv EpB, 14 mole percent oxygen, and 1.2 to 2.0 mole percent carbon dioxide (carbon dioxide partial pressure of 0.006 to 0.01 MPa).

The absorber off-gas was fed by means of lines 21 and 25 to the lower section of carbon dioxide absorber 40 which comprised a stainless steel column, 102 mm in diameter, packed with about 1.8 meters of 9.5 mm stainless steel Penn State packing. An aqueous alkanolamine solution comprising about 10–18 mole percent MEA and EBA was fed via conduit 41 to the upper section of the $CO_2$ absorber at a rate of about 190 ml per minute. The off-gas left the absorber via conduit 43 at a rate of about 173 standard liters per minute. The pressure and temperature in the absorber averaged about 0.52 MPa (75 psia) and 40° C. Alkanolamine solution rate and concentration was adjusted to maintain the $CO_2$ content of the outlet as in line 43 at less than about 100 ppmv of carbon dioxide.

A liquid comprising alkanolamine solution and $CO_2$-alkanolamine adduct was removed from the base of absorber 40 through conduit 49 and ed to the middle of adduct-decomposition column 60 comprising a stainless steel column, 50 mm in diameter, packed with about 1.8 meters of 9.5 mm stainless steel Berl saddles. A vapor was removed from the top of column 60 via line 65 and fed to heat exchanger 66 wherein the vapor was partially condensed against cooling water at a temperature of 40° C. An uncondensed vapor stream comprising carbon dioxide, oxygen, nitrogen, argon, and saturated with water and n-butane vapors was expelled from the system through line 67. Reflux was supplied via conduits 68 and 69 and the water balance was maintained by purging condensate via conduit 70. Reboiler 63 comprised a stainless steel column, 64 mm in diameter by 0.91 meter tall, containing a 6 mm diameter stainless steel heating coil. Heat was supplied by condensation in the heating coil of 0.63 MPa (90 psi) gage steam. Average reboiler temperature was 105 to 115° C. at a pressure of about 0.11 MPa. Regenerated alkanolamine solution was removed from column 60, piped via conduits 61, 71 and 72 to heat exchanger 73, cooled to about 40° C. and fed via lines 74 and 84 to carbon bed 85 comprising an 1.8 meter long by 25.4 mm diameter stainless steel pipe packed with about 920 cubic centimeters of Calgon Type F-300 8×30 mesh activated carbon. The filtered alkanolamine solution was removed from carbon bed 85 and recirculated via lines 86 and 76, tank 42 and line 41 to carbon dioxide absorber 40. The off-gas removed via conduit 43 from carbon dioxide absorber 40 was recycled to reactor via conduits 27,23, 2 and 4 and preheater 3.

The integrated reactor and recycle process as described above was operated continuously for about 4 weeks. The MEA/EBA solution inventory was maintained between about 10 and 20 weight percent of alkanolamines by periodic addition and partial purging of solution. Copper content in the alkanolamine solution was measured and maintained at the 150 ppm by weight level by the addition of a copper-based inhibitor as described in U.S. Pat. No. 4,477,419, incorporated herein by reference.

The average space-time yield (STY, pounds per hour per cubic foot of reactor volume), selectivity, conversion, and mole percent EpB in the reactor off-gas for the four weeks of operation are shown in Table 1. Throughout the four-week operation of the integrated process, the $CO_2$ content of $CO_2$ absorber off-gas in line 43 was less than about 100 ppmv $CO_2$.

When the MEA content of the alkanolamine solution dropped below about 6 weight percent and the EDBA content was above about 4.7 weight percent, the $CO_2$ content of the absorber off-gas was about 0.1 mole percent. Purging of a portion of the MEA-lean solution and addition of fresh MEA brought $CO_2$ removal back to previous levels. The average composition of the alkanolamine solution fed to $CO_2$ absorber 40 was 11.0–8.1% MEA, 0 to 7.7% EBA, 0–3.8% EDBA and 0–0.65% heat stable salts, wherein the percentages are by weight based on the total weight of the alkanolamine solution.

TABLE 1

| Example | STY | Conversion | Selectivity | % EpB in Effluent |
|---|---|---|---|---|
| 1 | 6.7 | 31 | 88 | 2.5 |
| C-1 | 5.9 | 27 | 90 | 2.2 |
| 2 | 7.5 | 35 | 88 | 2.8 |

Comparative Example C-1

This example illustrates the operation of an integrated epoxidation recycle gas process containing a carbon dioxide removal zone wherein a 30 weight percent potassium carbonate solution in water is the carbon dioxide absorbant. The process of Example 1 was repeated with the following modifications: carbon bed 85 was not used; average maximum temperature in epoxidation reactor 5 was 215° C. with an inlet temperature of 204° C.; average carbon dioxide content of the off-gas of conduit 43 from carbon dioxide absorber 40 was about 0.5 mole percent. The average space-time yield, selectivity, conversion, and mole percent EpB in the reactor off-gas during the course of Comparative Example C-1 are given in Table 1.

EXAMPLE 2

The process of Example 1 was repeated using 24 mole percent oxygen in the feed to the epoxidation reactor 5 during 6 hours of operation. The average space-time yield, selectivity, conversion, and mole percent EpB in the reactor off-gas are given in Table 1.

Comparative Example 2

The process of Example 1 was repeated except that the MEA concentration of the aqueous alkanolamine solution fed to the carbon dioxide absorber was allowed to drop below about 6 weight percent and EDBA concentration rose to about 5 weight percent. The carbon dioxide content of the carbon dioxide absorber off-gas rose to about 0.1 mole percent (1000 ppmv). The average composition of the alkanolamine solution fed to CO2 absorber 40 was 5.6% MEA, 10.3% EBA, 4.8% EDBA and 0.62% heat stable salts, wherein the percentages are by weight based on the total weight of the alkanolamine solution.

EXAMPLES 3–5

These examples compare the efficacy of monoethanolamine (MEA), 1-(2-hydroxyethylamino)-3-buten-2-ol (EBA), and (2-hydroxyethyl)-bis-(2-hydroxy-3-butenyl) amine (EDBA) as absorption solvents for carbon dioxide under temperature, pressure, and oxygen concentration conditions similar to those existing within a carbon dioxide absorber in an epoxidation process. For each of the Examples 3, 4 and 5, a stainless steel autoclave reactor of 100 mL capacity, fitted with a stirrer, temperature-controlled heating mantle, condenser, and vapor inlet and exit ports was loaded with 60.5 g of one of the following alkanolamine solutions: Example 3, 7 weight percent monoethanolamine in water; Example 4, 15 weight percent EBA in water; Example 5, 15 weight percent EDBA in water. In each example, the reactor was brought to 50° C. and pressurized to 0.41 MPa (60 psia) with helium. A gas flow of 130 standard cubic centimeters per minute (SCCM), consisting of 17 mole percent oxygen, 9 mole percent carbon dioxide, the balance helium was fed to the reactor. Pressure was maintained at 0.41 MPa (60 psia) by means of a back pressure regulator. The gas entered the shaft of the stirrer and intimately contacted the amine solution before exiting through the condenser outlet port.

The off-gas flow rate was measured approximately every 15 minutes and analyzed by an on-line gas chromatograph to determine the amount of carbon dioxide remaining in the gas. The experiment was continued until the carbon dioxide concentration in the inlet gas was equal to the carbon dioxide concentration in the outlet gas, an indication of equilibrium saturation of the amine solution with carbon dioxide. From this uptake data the equilibrium $CO_2$ capacity of each alkanolamine (moles of carbon dioxide per mole of alkanolamine) was determined to be:

| | |
|---|---|
| Example 3 | 0.45 |
| Example 4 | 0.43 |
| Example 5 | 0.13 |

EXAMPLES 6–9

These examples illustrate the relative oxidative degradation rates of MEA, EBA, and EDBA. The reactor system described in Examples 3–5 was used for Examples 6–9. After reaching equilibrium carbon dioxide saturation as described in Examples 3–5, the reactor temperature was raised to 110° C., the pressure to 0.31 MPa (45 psia),and the gas flow rate was changed to 100 SCCM at a 96/2/2 mole ratio of helium, oxygen, and carbon dioxide respectively, to simulate the conditions existing within the column wherein the $CO_2$-alkanolamine adduct is decomposed to $CO_2$ and alkanolamine stripper. The alkanolamine solutions used were: Example 6, 15 weight percent monoethanolamine in water; Example 7, 15 weight percent EBA in water; Example 8, 15 weight percent EDBA in water. Example 9, 15 weight percent monoethanolamine in water with copper inhibitor. A copper-based inhibitor as described in U.S. Pat. No. 4,477,419 was added at the 150 ppm by weight level in Example 9. No oxidative degradation inhibitor was added in Examples 6–8. An inhibitor level of 150 ppm was found to give the minimum rate of degradation for 15 weight percent aqueous MEA. Relative degradation rates for the alkanolamines in each of these examples are:

| | |
|---|---|
| Example 6 | 1.0 |
| Example 7 | 1.8 |
| Example 8 | 5.3 |
| Example 9 | 0.24 |

Example 10 and Comparative Examples 3 and 4

Example 10 and Comparative Examples 3 and 4 illustrate the effect of variable levels of carbon dioxide in the feed gas to a reactor for the vapor phase epoxidation of 1,3-butadiene to EpB. The epoxidation catalyst employed in these examples comprised an alumina support in the form of 6 mm outside diameter rings having deposited thereon 12 weight percent silver and 700 parts per million by weight (ppmv) cesium. The catalyst was prepared according to known procedures by impregnating the support material with solutions of a silver amine salt and cesium chloride followed by a thermal decomposition/reduction treatment in the presence of an oxygen-containing gas to convert the silver salt to silver metal.

The epoxidation reactions were carried out in a reactor tube fabricated from stainless steel tubing of 610 mm length with an inside diameter of 8.1 mm. The reactor tube was jacketed within a second stainless steel tube of 12.7 mm inside diameter provided with inlet and outlet ports for hot oil flow. The desired reactor temperature was maintained by adjusting hot oil flow though through the jacketing tube and by a temperature controller fitted to the hot oil reservoir. A portion of the above described silver/cesium/alumina catalyst rings was ground and sieved to provide catalyst granules having an irregular shape and a diameter ranging from about 1 to 0.71 mm. The reactor was charged with 12.6 g of these catalyst granules. The catalyst bed was 321 mm in length. The empty reactor volume above and below the catalyst bed was filled with Denstone ceramic particles of similar size to those of the catalyst to ensure that thermal reactions in such empty portions did not occur. A Chromel/-Alumel alloy thermocouple with four measurement points was embedded within the middle of the catalyst bed to measure reaction temperature. The measurement points were at −22 mm (i.e., in the Denstone pre-packing), 92 mm, 206 mm, 321 mm from the top of the catalyst bed.

The reactor was operated at three carbon dioxide feed levels corresponding to 0.0, 0.3 (3000 ppmv), and 0.6 mole percent (6000 ppmv) carbon dioxide. For each carbon dioxide feed level, the reactor was brought to steady state conditions at an inlet pressure of 0.12 MPa (17.9 psia) and an outlet pressure of 0.114 MPa (2.0 psia), with a maximum bed temperature of 190.2 to 190.3° C. The gaseous reactor feed consisting of n-butane, butadiene, oxygen in a 72/9/18 volumetric ratio, with 17.6 mole percent oxygen, was metered to the reactor using mass flow controllers. No carbon dioxide was co-fed in Example 10. Additional carbon dioxide was added to the reactor feed gas in Comparative Examples 3 and 4 as a standard mixture of 10 mole percent carbon dioxide in helium. The flow rate of the carbon dioxide/He mixture was adjusted to give an overall composition of 0.3 mole percent carbon dioxide and 0.6 mole percent carbon dioxide in Comparative Examples 3 and 4, respectively. The total flow rate was maintained at 500 standard cubic centimeters per minute for all three examples. Organic halide (2-chlorobutane) was added to the reactor feed gas in a stream of helium containing 100 parts per million by volume (ppmv) 2-chlorobutane to give an overall flow rate of 3 ppmv of 2-chlorobutane in the 500 SCCM of feed gas.

Analyses of the reaction products and feed compositions were performed using an in-line gas sampling loop connected directly to the inlet of a gas chromatograph. The conversion and selectivity achieved and the mole percent EpB in the epoxidation reactor (Mole% EpB) were:

| Example | Conversion | Selectivity | Mole % EpB |
|---|---|---|---|
| 10 | 20.3 | 92.3 | 1.70 |
| C-3 | 12.5 | 93.0 | 1.05 |
| C-4 | 9.1 | 92.9 | 0.76 |

EXAMPLE 11 and Comparative Example 5

These examples show the effect of operating pressure on the upper explosive limit of a n-butane/1,3-butadiene mixture. The pressure used in Comparative Example 5 corresponds to the recycle gas pressure required to make a hot potassium carbonate system function economically feasibly with low carbon dioxide partial pressure in the carbon dioxide absorber feed. Example 11 corresponds to an acceptable, although higher than required, recycle gas pressure for a monoethanolamine $CO_2$ removal system.

The upper explosive limit was calculated by LeChatlier's Rule from pure component explosive limit measurements for a 8/1 molar mixture of n-butane/1,3-butadiene with 10 mole percent added helium. Two calculations were made. At 85° C. and 0.655 MPa (95 psia), Comparative Example 5, the maximum safe oxygen concentration at the upper explosive limit of the mixture was calculated to be 24 mole percent oxygen. At 85° C. and 0.345 MPa (50 psia), Example 11, the maximum safe oxygen concentration at the upper explosive limit of the mixture was calculated to be 31 mole percent oxygen.

EXAMPLE 12 and Comparative Example 6

The same reactor system and catalyst as described in Example 10 were used to determine the effect of oxygen concentration on the vapor phase epoxidation of 1,3-butadiene to 3,4-epoxy-1-butene. Gaseous n-butane, butadiene, 2-chorobutane in helium were fed as in Example 10 and the n-butane/butadiene molar ratio was maintained at 8/1. The reactor was operated at two oxygen feed levels, 18 and 24 mole percent oxygen, Comparative Example 6 and Example 12, respectively, corresponding to approximately 75 percent of the maximum safe oxygen levels determined in Comparative Example 5 and Example 11. For each oxygen feed level, the reactor was brought to steady state conditions with an inlet pressure of 0.12 MPa (17.9 psia) and an outlet pressure of 0.114 MPa (2.0 psia), with a maximum bed temperature of 190.2 to 190.3° C. The total flow rate of all feed components was maintained at 500 SCCM by adjusting the butane/butadiene flow rates to compensate for the change in oxygen flow, The conversion and selectivity achieved and the mole percent EpB in the epoxidation reactor (Mole% EpB) were:

| Example | Conversion | Selectivity | Mole % EpB |
|---------|------------|-------------|------------|
| 12      | 23.2       | 91.8        | 1.92       |
| C-6     | 20.3       | 92.3        | 1.70       |

EXAMPLE 13

This example illustrates the removal of residual EpB from a simulated EpB absorber off-gas stream by absorption into an aqueous phosphoric acid gas solvent. The absorption of EpB was carried out in a jacketed glass column, 762 mm long and 25.4 mm inside diameter. The secondary EpB absorption column was packed with 762 mm of Hastalloy Goodloe structured packing. The column temperature was maintained at 50° C. throughout the experiment by circulating a mixture of water and ethylene glycol from a temperature-controlled reservoir through the jacket. The column was fitted with top and bottom liquid and vapor inlet and outlet ports. An 0.1 molar aqueous phosphoric acid solution was pumped at a rate of 30 cc per minute from a heated 1000 mL glass reservoir to the upper liquid inlet port of the column. The liquid was contacted countercurrently by a gaseous mixture of n-butane, helium, and EpB vapor. The gaseous feed mixture was metered by mass flow controllers at a total rate of 960 standard cubic centimeters per minute (SCCM) to the lower vapor inlet port of the column. EpB concentration in the inlet gas was 1730 ppmv, confirmed by an on-line gas chromatograph.

EpB, a liquid at ambient temperatures, was fed to the absorption column by means of a helium-swept vapor-liquid equilibrium cell. The VLE cell consisted of a jacketed 500 mL stainless steel vessel fitted with a vapor inlet port and connected dip tube extending almost to the bottom of the cell, and a vapor outlet port. The VLE cell was filled to approximately 80 percent of capacity with EpB, leaving some head space for equilibration and vapor-liquid disengagement. The position of the vapor inlet tube forced the sweep gas, i.e., helium, to pass through the body of the liquid and become saturated with EpB, before exiting the cell through the vapor outlet port. The feed rate of diluent was controlled by varying the helium sweep rate and the jacket temperature. The VLE temperature was set at 25° C., with a helium flowrate of 6.85 SCCM. Under these conditions, the 6.85 SCCM swept out 1.66 SCCM of EpB. The remainder of the inlet gas, i.e., 951.5 SCCM, was n-butane.

The secondary EpB absorber was allowed to come to steady-state operation and analysis of the outlet gas stream by an on-line gas chromatograph indicated that the EpB concentration was less than 10 ppmv, giving 99.4 percent removal efficiency. Gas residence time in the column was about 22 seconds.

EXAMPLES 14–15 and Comparative Examples 7–8

The same reactor system as described in Example 10 was used to determine the effect of MEA on the operation of the epoxidation reactor. The reactor was loaded with 12.02 g of silver/cesium/alumina. The catalyst was ground and sieved to granules of diameters between 1.0 and 0.71 mm. For Example 14, the catalyst was brought on line with a flow rate of 3000 standard cubic centimeters (SCCM) of 9 mole percent 1,3-butadiene, 18 mole percent oxygen, 10 mole percent argon, 63 mole percent n-butane, and 1 ppmv 2-chlorobutane. The catalyst reached steady state after about 20 hours of operation with a maximum bed temperature of about 200° C. The catalyst remained at steady state conditions for eight days. Average conversion was about 17.7 percent at a selectivity of about 93.5 percent for the eight days of steady state operation.

For Comparative Example 7, at the end of eight days of steady state operation, monoethanolamine was added to the feed gas at the rate of 12 ppmv via the vapor-liquid equilibrium cell described in Example 13. All other gas flows and the maximum bed temperature were maintained at previous values. The selectivity and conversion initially increased for the first two days of operation, but then activity rapidly declined and fell to zero within four days of operation.

For Example 15, the MEA feed was removed, all other values remained constant. Within 24 hours, productivity has reached former levels with a selectivity of 93.3 percent and conversion of 17.2 percent.

For Comparative Example 8, 12ppm MEA was reintroduced into the gas feed, all other values remained constant. Within 24 hours, productivity had fallen to zero.

EXAMPLE 16 and Comparative Examples 9–10

The same reactor system as described in Example 10 was used to determine the effect of diethanolamine (DEA) on the operation of the epoxidation reactor. The reactor was loaded with 12.0 g of silver/cesium/alumina catalyst. The catalyst was ground and sieved to granules of diameters between 1.0 and 0.71 mm.

For Example 19, the catalyst was brought on line with a flow rate of 3000 standard cubic centimeters (SCCM) of 9 mole percent 1,3-butadiene, 18 mole percent oxygen, 10 mole percent argon, 63 mole percent n-butane, and 1 ppmv 2-chlorobutane. The catalyst reached steady state after about 40 hours of operation with a maximum bed temperature of about 202° C. The catalyst remained at steady state conditions for five days. Average conversion was about 19.4 percent at a selectivity of 93.7 percent for the five days of steady state operation.

For Comparative Example 9, at the end of five days of steady state operation, diethanolamine was added to the feed gas at the rate of 0.5 ppmv via the vapor-liquid equilibrium cell described in Example 13. All other gas flows and the maximum bed temperature were maintained at previous values. No effect was seen after four days. The DEA rate was increased to 1.5 ppmv. Activity gradually began to decline after an additional 4 days of operation and had reached zero activity after 3 more days of operation.

For Comparative Example 10, the DEA feed was removed, all other values remained constant. No catalyst activity was seen. The catalyst was permanently deactivated by the DEA.

The invention has been described in detail with particular reference to preferred embodiments thereof, but it will be understood that variations and modifications may be effected within the spirit and scope of the invention.

We claim:

1. Process for the removal of carbon dioxide from a butadiene epoxidation effluent recycle gas stream comprising about 3 to 15 mole percent butadiene, about 8 to 25 mole percent oxygen, about 55 to 88 mole percent inert diluent gas and about 0.5 to 10 mole percent carbon dioxide which comprises feeding the gas stream to an absorption vessel wherein the gas stream is intimately contacted with a liquid solution of an alkanolamine at a pressure of about 0.1 to 1 MPa and a temperature of about 20 to 65° C. to obtain:

(1) a vapor effluent comprising butadiene, oxygen, inert diluent gas and about 0.005 to 0.5 mole percent carbon dioxide from the upper section of the absorption vessel; and (2) a liquid effluent comprising the alkanolamine solution and carbon dioxide-alkanolamine adduct from the lower section of the absorption vessel;

wherein butadiene is 1,3-butadiene.

2. Process according to claim 1 wherein the liquid solution of alkanolamine comprises a solution of at least one primary or secondary alkanolamine containing up to about 10 carbon atoms and having a boiling point of less than about 250° C. in water, an alkanol, a glycol or a mixture of any two or more thereof.

3. Process according to claim 2 wherein said alkanolamine is selected from the group consisting of monoethanolamine; 2-amino-2-methyl-1-propanol, 3-amino-3-methyl-2-pentanol, 2,3-dimethyl-3-amino-1-butanol, 2-amino-2-ethyl-1-butanol, 2-amino-2-methyl-3-pentanol, 2-amino-2-methyl-1-butanol, 2-amino-2-methyl-1-pentanol, 3-amino-3-methyl-1-butanol, 3-amino-3-methyl-2-butanol, 2-amino-2,3-dimethyl-1-butanol, 1-amino-3-buten-2-ol, 2-amino-3-buten-1-ol, 1-aminobutan-2-ol, 2-amino-butan-1-ol, diethanolamine, 2-(ethylamino)-ethanol, 2-(methylamino)-ethanol, 2-(propylamino)ethanol, 2-(isopropylamino)ethanol, 2-(butylamino)ethanol, 1-(ethylamino)ethanol, 1-(methylamino)-ethanol, 1-(propylamino)ethanol, 1-(isopropylamino)ethanol, and 1-(butylamino)-ethanol, 1-methylamino-3-buten-2-ol, 2-methylamino-3-buten-1-ol, 1-ethylamino-3-buten-2-ol, 2-ethylamino-3-buten-1-ol, 1-propylamino-3-buten-2-ol, 2-propylamino-3-buten-1-ol, 1-butylamino-3-buten-2-ol, 2-butylamino-3-buten-1-ol.

4. Process for the removal of carbon dioxide from a butadiene epoxidation effluent recycle gas stream about 3 to 15 mole percent butadiene, about 8 to 25 mole percent oxygen, about 55 to 88 mole percent inert diluent gas and about 0.5 to 10 mole percent carbon dioxide which comprises the steps of:

(I) feeding the gas stream to a first absorption vessel wherein the gas stream is intimately contacted with a liquid solution of an alkanolamine at a pressure of about 0.1 to 1 MPa (14.5 to 145 psia) and a temperature of about 20 to 65° C. to obtain:

(i) a vapor effluent comprising butadiene, oxygen, inert diluent gas, about 0.005 to 0.5 mole percent carbon dioxide from the upper section of the absorption vessel, and about 20 to 2000 ppmv alkanolamine; and (ii) a liquid effluent comprising the alkanolamine solution and carbon dioxide-alkanolamine adduct from the lower section of the first absorption vessel; and (II) feeding vapor effluent (i) to a second absorption vessel wherein the gas stream is intimately contacted with a solvent at a pressure of about 0.1 to 1.1 MPa and a temperature of about 20 to 65° C. to obtain:

(iii) a vapor effluent comprising butadiene, oxygen, inert diluent gas, about 0.005 to 0.5 mole percent carbon dioxide from the upper section of the absorption vessel, and less than 10 ppmv alkanolamine; and (iv) a liquid effluent comprising solvent and absorbed alkanolamine from the lower section of the absorption vessel; wherein butadiene is 1,3-butadiene.

5. Process according to claim 4 wherein the liquid solution of alkanolamine comprises a solution of at least one primary or secondary alkanolamine containing up to about 10 carbon atoms and having a boiling point of less than about 250° C. in water, an alkanol, a glycol or a mixture of any two or more thereof and the solvent of step (II) comprises water, an alkanol, a glycol or a mixture of any two or more thereof.

6. Process according to claim 4 wherein the liquid solution of alkanolamine comprises a solution of at least one primary or secondary alkanolamine in water, an alkanol, a glycol or a mixture of any two or more thereof wherein the alkanolamine is selected from the group consisting of monoethanolamine, 2-amino-2-methyl-1-propanol, 3-amino-3-methyl-2-pentanol, 2,3-dimethyl-3-amino-1-butanol, 2-amino-2-ethyl-1-butanol, 2-amino-2-methyl-3-pentanol, 2-amino-2-methyl-1-butanol, 2-amino-2-methyl-1-pentanol, 3-amino-3-methyl-1-butanol, 3-amino-3-methyl-2-butanol, 2-amino-2,3-dimethyl-1-butanol, 1-amino-3-buten-2-ol, 2-amino-3-buten-1-ol, 1-aminobutan-2-ol, 2-amino-butan-1-ol, diethanolamine, 2-(ethylamino)-ethanol, 2-(methylamino)ethanol, 2-(propylamino)ethanol, 2-(isopropyl-amino)ethanol, 2-(butylamino)-ethanol, 1-(ethylamino)ethanol, 1-(methylamino)-ethanol, 1-(propylamino)ethanol, 1-(isopropylamino)-ethanol, and 1-(butylamino)-ethanol, 1-methylamino-3-buten-2-ol, 2-methylamino-3-buten-1-ol, 1-ethylamino-3-buten-2-ol, 2-ethylamino-3-buten-1-ol, 1-propylamino-3-buten-2-ol, 2-propylamino-3-buten-1-ol, 1-butylamino-3-buten-2-ol, and 2-butylamino-3-buten-1-ol; the solvent of step (II) comprises water, an alkanol, a glycol or a mixture of any two or more thereof; the concentration of CO2 of vapor effluent (i) is about 0.005 to 0.1 mole percent; the concentration of alkanolamine in vapor effluent (i) is less than 5.0 ppmv; and vapor effluent (iii) is recycled to an epoxidation process wherein butadiene is contacted with an oxygen-containing gas in the presence of a silver catalyst.

7. Process according to claim 6 wherein the alkanolamine is monoethanolamine.

8. Process according to claim 6 wherein the alkanolamine is 2-amino-2-methyl-1-propanol.

9. Process according to claim 6 wherein the alkanolamine is 2-(ethylamino)-ethanol.

10. Process according to claim 6 wherein the alkanolamine is 1-amino-3-buten-2-ol or 2-amino-3-buten-1-ol.

11. Process according to claim 6 wherein the liquid solution of alkanolamine comprises a solution of at least one primary or secondary alkanolamine in a solvent is selected from the group consisting of butanol, pentanol, hexanol, ethylene glycol, propylene glycol, butylene glycol, 1-butene-3,4-diol, and 2-butene-1,4-diol.

12. Process according to claim 6 wherein the liquid solution of alkanolamine comprises a solution of at least one primary or secondary alkanolamine in water.

13. Process according to claim 4 wherein the concentration range of alkanolamine or mixture of alkanolamines is 7 to 65 weight percent alkanolamine.

14. The process of claim 4 wherein the alkanolamine is monoethanolamine or a mixture of monoethanolamine and 1-(2-hydroxyethylamino)-3-buten-2-ol and the concentration of the alkanolamine is 10 to 45 weight percent.

15. Process according to claim 14 wherein the concentration of alkanolamine is 12 to 35 weight percent in water.

16. Process according to claim 4 wherein the alkanolamine is 2-amino-2-methyl-1-propanol and the solution concentration is 15 to 40 weight percent in water.

17. Process according to claim 4 wherein the alkanolamine solution flow rate is set to give a carbon dioxide:alkanolamine molar ratio within said carbon dioxide absorption zone of 0.25 to 1.0 moles carbon dioxide per mole of alkanolamine.

18. Process according to claim 4 wherein the alkanolamine solution flow rate is set to give a carbon dioxide:alkanolamine molar ratio of 0.25 to 0.65 moles/mole, and wherein said alkanolamine is monoethanolamine or a mixture of monoethanolamine and 1-(2-hydroxyethylamino)-3-buten-2-ol.

19. Process according to claim 4 wherein the alkanolamine solution flow rate is set to give a carbon dioxide:alkanolamine molar ratio of 0.35 to 0.45 moles/mole, and wherein said alkanolamine is monoethanolamine or a mixture of monoethanolamine and 1-(2-hydroxyethylamino)-3-buten-2-ol.

20. Process according to claim 4 wherein the alkanolamine solution flow rate is set to give a carbon dioxide:alkanolamine molar ratio of 0.35 to 0.7 moles/mole, and wherein said alkanolamine is 2-amino-2-methyl-1-propanol.

21. Process according to claim 4 wherein the pressures of the first and second absorption vessels are within the range of about 0.2–0.9 MPa.

22. Process for the removal of carbon dioxide from a butadiene epoxidation effluent recycle gas stream comprising about 3 to 15 mole percent butadiene, about 8 to 25 mole percent oxygen, about 55 to 88 mole percent inert diluent gas and about 0.5 to 10 mole percent carbon dioxide which comprises the steps of:

(I) feeding the gas stream to an absorption vessel wherein the gas stream is intimately contacted with a liquid solution of an alkanolamine at a pressure of about 0.1 to 1 MPa and a temperature of about 20 to 65° C. to obtain:

(i) a vapor effluent comprising butadiene, oxygen, inert diluent gas and about 0.005 to 0.5 mole percent carbon dioxide from the upper section of the absorption vessel; and (ii) a liquid effluent comprising the alkanolamine solution and carbon dioxide-alkanolamine adduct from the lower section of the absorption vessel; and (II) subjecting liquid effluent (ii) to an alkanolamine reclamation process which comprises feeding liquid effluent (II) to the lower section of a column wherein the liquid is heated at a temperature of about 90 to 165° C. to obtain:

(iii) a vapor effluent comprising carbon dioxide from the upper section of (iv) a liquid effluent comprising the alkanolamine solution substantially free of carbon dioxide-alkanolamine adduct from the lower section of the column; wherein butadiene is 1,3-butadiene.

23. Process according to claim 22 wherein the liquid solution of alkanolamine comprises a solution of at least one primary or secondary alkanolamine in water, an alkanol, a glycol or a mixture of any two or more thereof wherein the alkanolamine is selected from the group consisting of monoethanolamine, 2-amino-2-methyl-1-propanol, 3-amino-3-methyl-2-pentanol, 2,3-dimethyl-3-amino-1-butanol, 2-amino-2-ethyl-1-butanol, 2-amino-2-methyl-3-pentanol, 2-amino-2-methyl-1-butanol, 2-amino-2-methyl-1-pentanol, 3-amino-3-methyl-1-butanol, 3-amino-3-methyl-2-butanol, 2-amino-2,3-dimethyl-1-butanol, 1-amino-3-buten-2-ol, 2-amino-3-buten-1-ol, 1-aminobutan-2-ol, 2-amino-butan-1-ol, diethanolamine, 2-(ethylamino)-ethanol, 2-(methylamino)ethanol, 2-(propylamino)ethanol, 2-(isopropyl-amino)ethanol; 2-(butylamino)-ethanol, 1-(ethylamino)ethanol, 1-(methylamino)-ethanol, 1-(propylamino)ethanol, 1-(isopropylamino)-ethanol, and 1-(butylamino)-ethanol, 1-methylamino-3-buten-2-ol, 2-methylamino-3-buten-1-ol, 1-ethylamino-3-buten-2-ol, 2-ethylamino-3-buten-1-ol, 1-propylamino-3-buten-2-ol, 2-propylamino-3-buten-1-ol, 1-butylamino-3-buten-2-ol, and 2-butylamino-3-buten-1-ol.

24. Process according to claim 22 wherein step (II) comprises subjecting liquid effluent (ii) to an alkanolamine reclamation process which comprises heating liquid effluent (ii) at a temperature of about 65 to 90° C. and at a pressure of 0.1 to 0.35 Mpa to remove dissolved gases from the liquid and then feeding the liquid to the lower section of a column wherein the liquid is heated at a temperature of about 90 to 165° C.

* * * * *